United States Patent [19]
Petreto

[11] Patent Number: 5,938,663
[45] Date of Patent: Aug. 17, 1999

[54] SPINAL INSTRUMENTS, PARTICULARLY FOR A ROD

[75] Inventor: Eric Petreto, Cestas, France

[73] Assignee: Stryker France, S.A., France

[21] Appl. No.: 08/930,438

[22] PCT Filed: Mar. 5, 1996

[86] PCT No.: PCT/FR96/00342

§ 371 Date: Sep. 5, 1997

§ 102(e) Date: Sep. 5, 1997

[87] PCT Pub. No.: WO96/27340

PCT Pub. Date: Sep. 12, 1996

[30] Foreign Application Priority Data

Mar. 6, 1995 [FR] France .................................. 95 02580

[51] Int. Cl.⁶ .................................................. A61B 17/70
[52] U.S. Cl. ................................................. 606/61; 606/73
[58] Field of Search .................. 606/61, 60, 72, 606/73; 623/17

[56] References Cited

U.S. PATENT DOCUMENTS

| | | | |
|---|---|---|---|
| 4,771,767 | 9/1988 | Steffee | 606/61 |
| 5,222,954 | 6/1993 | Baker et al. | 606/61 |
| 5,282,862 | 2/1994 | Baker et al. | 623/17 |
| 5,352,226 | 10/1994 | Lin | 606/61 |
| 5,501,684 | 3/1996 | Schlapfer et al. | 606/73 |
| 5,520,689 | 5/1996 | Schlapfer et al. | 606/61 |

FOREIGN PATENT DOCUMENTS

| | | |
|---|---|---|
| 0 567 423 | 4/1993 | European Pat. Off. . |
| 585518 | 3/1994 | European Pat. Off. . |
| 2693365 | 1/1994 | France . |

*Primary Examiner*—Guy V. Tucker
*Attorney, Agent, or Firm*—Blakely Sokoloff Taylor & Zafman

[57] ABSTRACT

The invention relates to a spinal instrument for essentially smooth adjustable connecting rods. The spinal instrument has a nut (5) that clamps receiving and locking assembly (8) to a multi-threaded bone anchor member (1). The receiving and locking assembly (8) has a compressible ring (24) disposed within a clamp (9) having a lower branch (10) and an upper branch (11) coupled between a connecting area (12). The connecting rod fits into the compressible ring (24). With the cavity-ring assembly forming a ball joint, the connecting rod may be clamped into the required angular position. Other features are disclosed.

17 Claims, 4 Drawing Sheets

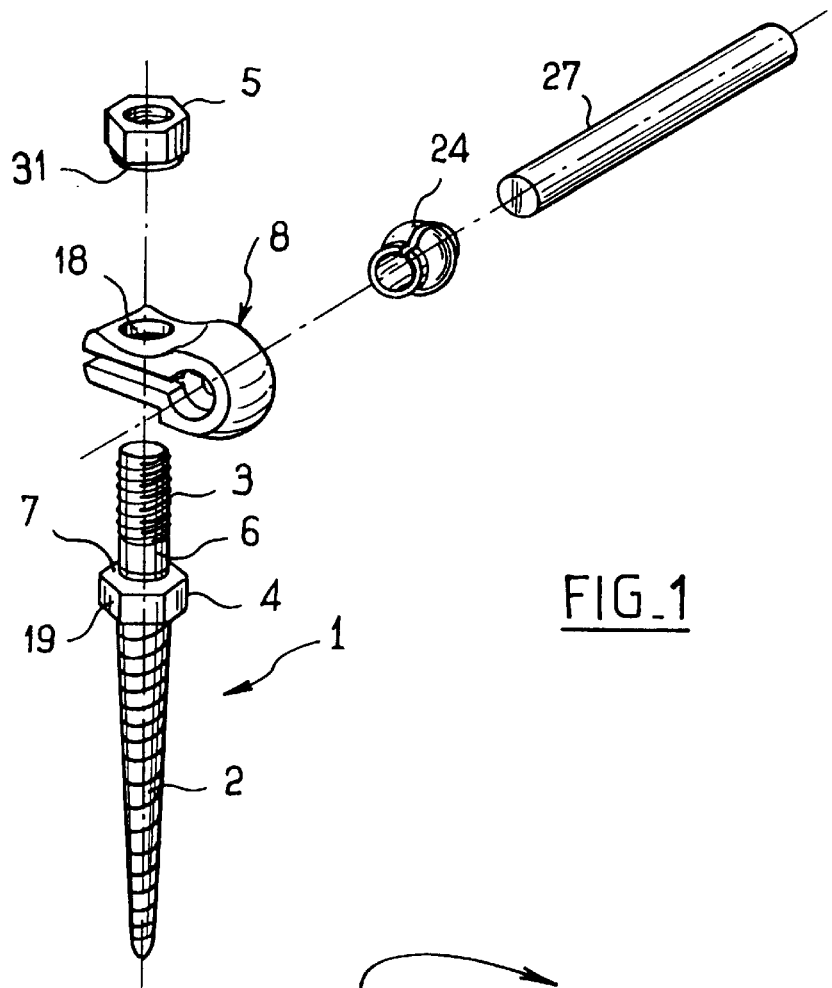
FIG_1
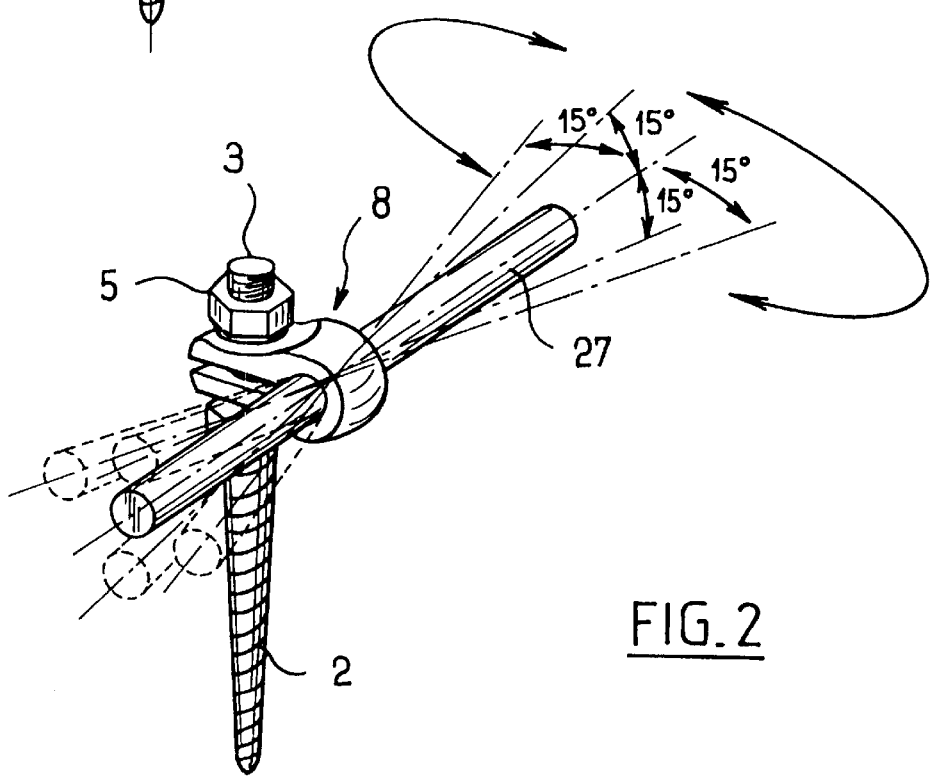
FIG_2

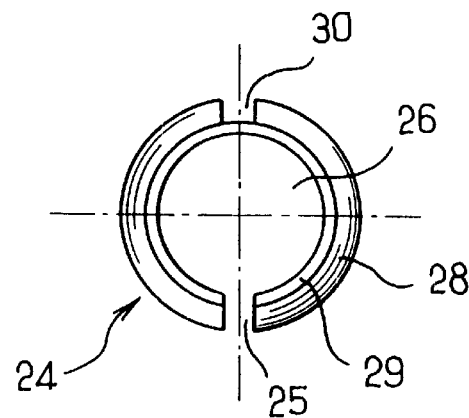
FIG_6
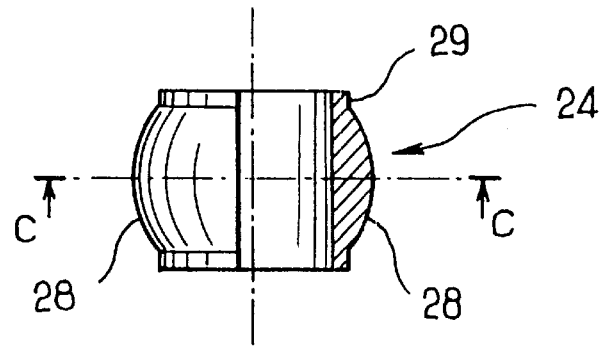
FIG_7
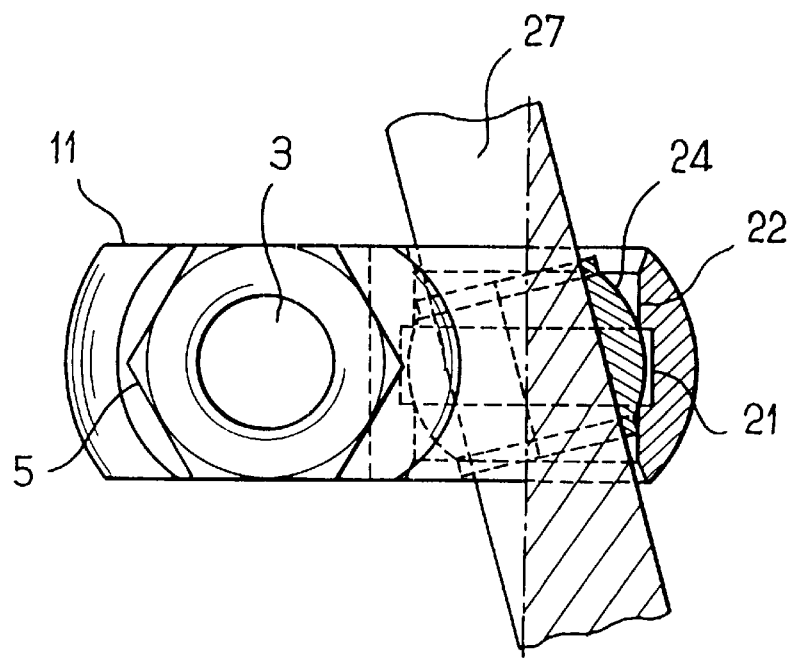
FIG_8

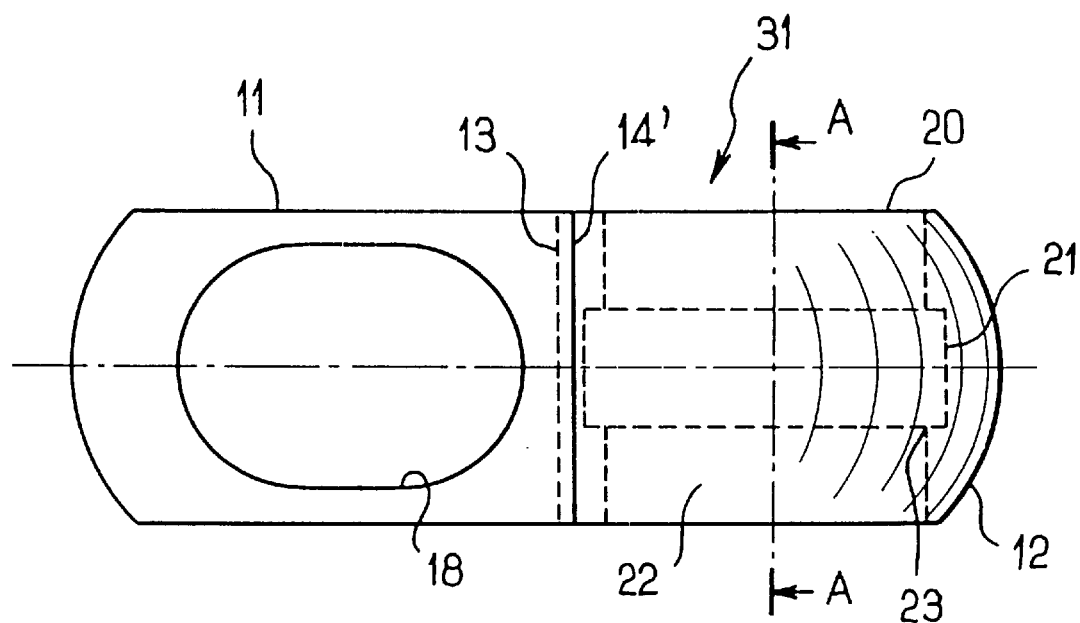
FIG_9
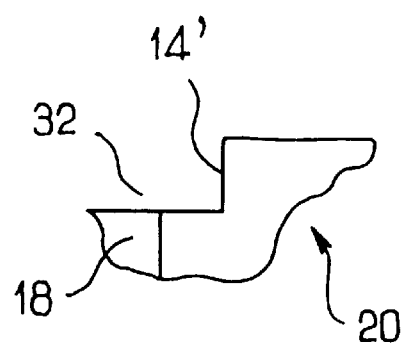
FIG_10

SPINAL INSTRUMENTS, PARTICULARLY FOR A ROD

This application is filed under 35 U.S.C. 371 based on PCT/FR96/00342, filed on Mar. 5, 1996.

BACKGROUND OF THE INVENTION

1. Field of the Invention

The present invention relates to spinal instruments, especially for essentially smooth connecting rods comprising a bone anchor member having an anchor part separated from a projecting screwthreaded head, associated with a nut, by a polygonal section intermediate body, enabling screwing in the case where the anchor part is a screw and forming an abutment in its upper part, and a receiving and locking assembly adapted to receive said rod.

It also relates to a receiving and locking assembly adapted in particular to connect a rod to an anchor member.

2. Prior Art

Patent FR-2 657 775 describes rod type spinal instruments adapted to reduce and to contain the spine, comprising a grub screw with a screwthreaded cylindrical head receiving a part engaged on a screwthreaded head enabling locking of a connecting rod between a bearing portion of said part and the conical portion of a locknut engaged on the screwthreaded head.

This system locks the rod relative to the screws, but the orientation of the rod relative to the screw, which is orthogonal to the screw, is the same for all of the screws and cannot be modified.

French patent 2 693 365 describes rod type spinal instruments allowing some degree of adjustment of the angle between the respective axes of the rod and of the screw in a particular plane (i.e. without this plane being able to pivot about the axis of the rod) and locking of the rod to the screw in this position.

This device comprises a grub screw with a screwthreaded head having an intermediate body, a receiving and locking assembly engaged on said screwthreaded head by means of an oblong orifice and provided with a housing to receive the rod laterally of the screw and abutting on the spherical shape upper surface of the intermediate body. The frustoconical lower face of the nut screwed onto the screwthreaded head comes into contact, in an area opposite the area of contact with the rod, with a corresponding frustoconical surface on said receiving and locking assembly.

It is nevertheless desirable to have a receiving and locking assembly enabling the angle of the rod relative to the screw to be increased and thereby to reduce further the curvature of the rods and consequently the tension in the arrangement linking the various grub screws, whilst significantly improving the locking and therefore the rigidity of the assembly.

Document U.S. Pat. No. 5,222,954 describes spinal instruments for connecting rods in which the receiving and locking part 26 is in the form of an orifice 28 enabling the engagement of a projecting screwthreaded head 16 and a second orifice 34 the axis of which is perpendicular to the axis of the orifice 28 and which is adapted to receive the connecting rod 40. Note that this device does not allow the connecting rod to be oriented in all directions, which is possible with the device of the present invention.

Likewise, documents EP-A-585 518 and U.S. Pat. No. 5,352,226 do not allow the connecting rod to be oriented in all directions.

Document U.S. Pat. No. 4,771,767 requires the use of a screwthreaded rod, which has the disadvantage that it cannot be modified to adapt it to the deformation or to the anatomy of the spine.

The aim of the present invention is therefore to propose spinal instruments featuring improved locking of the connecting rod whilst allowing the rod to be oriented in all directions within a certain angle relative to the neutral axis.

BRIEF SUMMARY OF THE INVENTION

The invention relates to a spinal instrument for essentially smooth adjustable connecting rods. The spinal instrument has a nut (5) that clamps receiving and locking assembly (8) to a multi-threaded bone anchor member (1). The receiving and locking assembly (8) has a compressible ring (24) disposed within a clamp (9) having a lower branch (10) and an upper branch (11) coupled between a connecting area (12). The connecting rod fits into the compressible ring (24). With the cavity-ring assembly forming a ball joint, the connecting rod may be clamped into the required angular position. Other features are disclosed.

BRIEF DESCRIPTION OF THE DRAWINGS

Features and advantages will emerge from the following description of one embodiment of the device of the invention given by way of example and with reference to the accompanying drawings, in which:

FIG. 1 is an exploded perspective view of a device of the invention;

FIG. 2 is a perspective view of an assembled device of the invention;

FIG. 6 is an end view of another portion of the device;

FIG. 7 is a half-sectional view of the portion from FIG. 6 taken along the line CC;

FIG. 8 is a part-sectional view of the implant when assembled and locked;

FIG. 9 is a top view of a variant of the portion from FIGS. 3 through 5; and

FIG. 10 is a part-sectional view of the portion from FIG. 9.

DETAILED DESCRIPTION OF THE INVENTION

Figure 3:
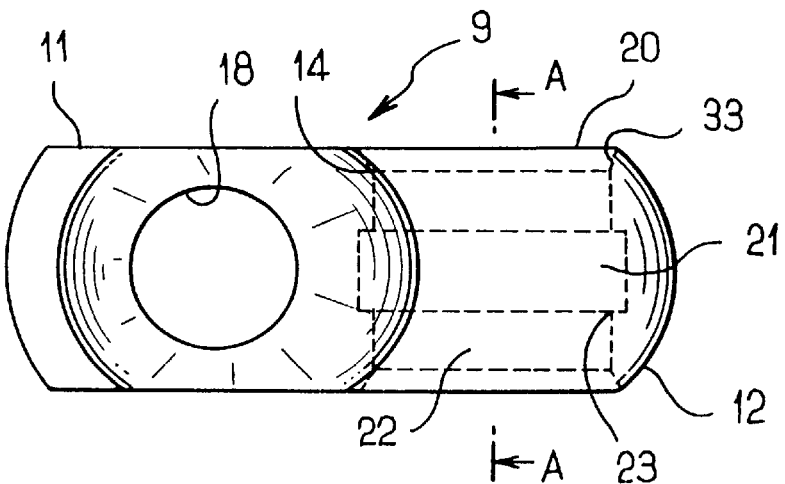
FIG. 3 is a top view of a portion of the device at rest.

The invention is characterized in that said receiving and locking assembly comprises:

a member forming a clamp having two branches linked by a connecting area, the branches being provided with aligned orifices through which the screwthreaded head can be passed as far as the abutment and the clamp delimiting a cavity between the branches;

a compressible ring housed in the cavity and having a central passage to receive the connecting rod, the cavity-ring assembly forming a ball joint so that the clamping of the branches by means of the nut engaged on the screwthreaded head locks the ring and the connecting rod in the required angular position.

The spinal instruments are made of a biocompatible material for surgical implantation such as stainless steel or a titanium-based alloy.

In a manner that is known in itself, the bone anchor members can be grub screws or hooks. other anchor means can be used in the context of the present invention.

The "screwthreaded rod" is an essentially smooth member, i.e. it can slide freely through the ring before it is clamped.

The rod can be a smooth connecting member of sufficient diameter to resist the stresses and loads of the spine, a smooth surface having the advantage that it can be modified to attain some degree of curvature matching the deformation or the anatomy of the spine. The rod can equally well comprise braided flexible cylindrical wires.

To facilitate the task of the surgeon, it is advantageous to limit the angle of the axis of the ring relative to the axis of the cavity at rest. This facilitates insertion of the rod because the passage is always accessible. One advantageous solution is to provide the ring with one or more abutments limiting its rotation.

To improve the locking of the ring it is advantageous to provide appropriate additional means to accentuate the pressure applied at certain points on the ring by the cavity. The cavity is therefore preferably provided with at least one sharp edge adapted to load the ring. This can be a groove in the cavity providing two other sharp edges bearing on the ring in the locked position. The quality of clamping can also be improved by at least partially roughening the surface of the cavity and that of the ring by sandblasting or machining.

To improve locking further, the nut has a spherical convex lower face that fits to a spherical concave area around the orifice on the corresponding branch.

The ring is advantageously annular, preferably spherical, and has a convex exterior face the diameter of which is between that of a depressed central portion and that of lateral portions of the cavity.

The compressibility of the ring is preferably assured by a through-slot. Flexibility can be further improved by a groove symmetrically opposite the slot.

Referring to FIG. 1, a grub screw 1 has a screwthreaded lower portion or point 2 adapted to penetrate a vertebral body and a screwthreaded upper portion or head 3 onto which a nut 5 can be screwed. The point 2 and the head 3 are separated by an intermediate body 4, of hexagonal section having vertical faces 19 in the embodiment shown, enabling the point 2 to be screwed in using a wrench.

The screwthreaded head 3 is separated from the intermediate body 4 by a smooth portion 6 the diameter of which corresponds to the root diameter of the screw thread of the head 3, for example. The intermediate body 4 has a plane upper surface forming an abutment 7.

Figure 4:
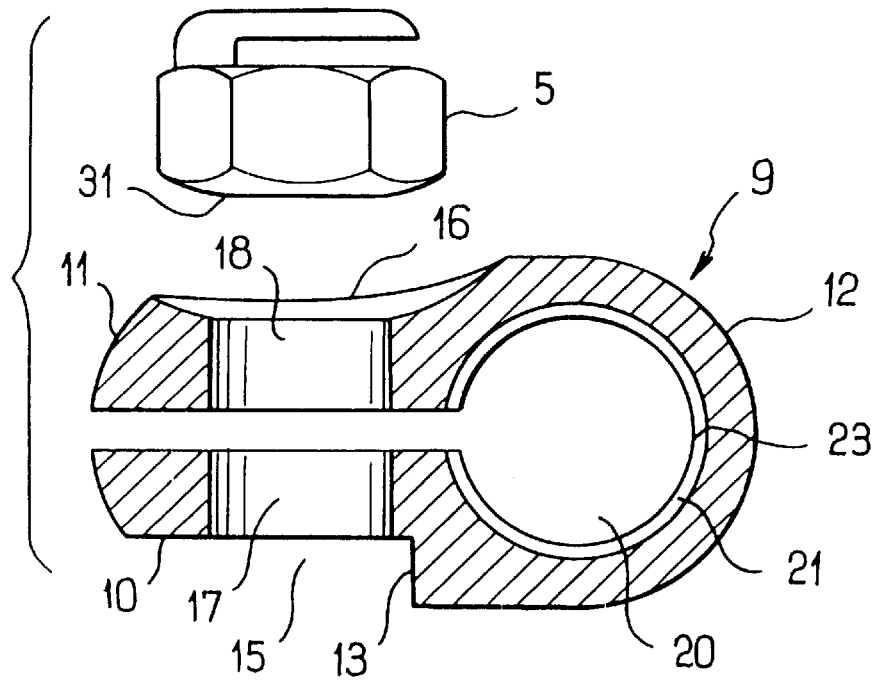
FIG. 4 is a sectional view taken along the line III—III of the portion shown in FIG. 3.
Figure 5:
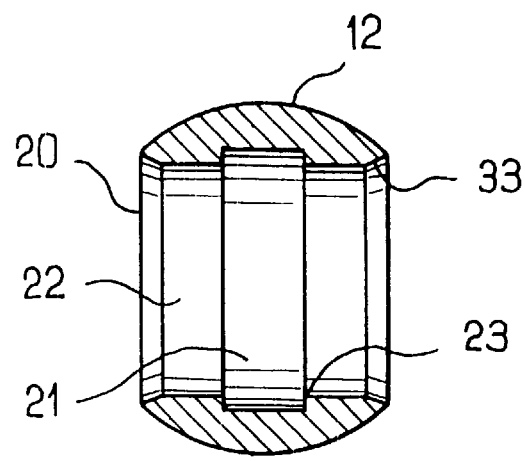
FIG. 5 is a sectional view taken along the line AA of the portion shown in FIGS. 3 and 4.

FIGS. 3, 4 and 5 show a part forming a clamp 9 which is a portion of a receiving and locking assembly 8 of the device. The clamp 9 has lower and upper branches 10 and 11 and a connecting area 12 linking these branches. The external face of the lower branch 10 has a straight step 13 delimiting a lower recessed external area 15. The external face of the upper branch 11 has a curved edge 14 delimiting a concave spherical recessed area 16 centered on the orifice 18. The branches 10 and 11 have coaxial orifices 17 and 18 of appropriate diameter aligned to allow insertion of the screwthreaded head 3 as far as the abutment 7 so as to permit a vertical face 19 of the intermediate body 4 to bear on the lower step 13, thus preventing any relative rotation of the grub screw 1 and the clamp 9. The nut 5 has a spherical convex lower face 31 which fits to the concave area 16.

The clamp 9 delimits an interior cavity 20 open on both sides of the clamp. Interior cavity 20 has a cylindrical central portion 21 flanked on each side by two cylindrical lateral portions 22 with a smaller radius, the three portions being coaxial. The steps due to the greater radius of the central portion 21 provide two circular sharp edge 23. The external edge of each cylindrical lateral portion 22 preferably has a chamfer 33 to facilitate insertion of the rod 27 and so as not to impede its freedom of angular movement.

Referring to FIGS. 6 through 8, the interior cavity 20 houses a ring 24 the length of which is preferably less than that of the interior cavity 20 and which is provided with a straight through-slot 25. The ring 24 receives in its interior passage 26 a cylindrical connecting rod 27. The external face of the ring has a central spherical enlargement 28 the top of which is inserted in the unclamped position of the clamp 9 into the interior cavity 20 delimited by the central portion 21, the spherical enlargement 28 being extended on each side by two externally cylindrical portions 29 forming annular abutments so that, in the unlocked position, the angle of the axis of the ring 24 is limited by the annular abutments bearing on the walls of cylindrical lateral portion 22 of the interior cavity 20. A groove 30 in the spherical enlargement 28 symmetrical to the slot 25 improves the flexibility of the ring.

Note here that the diameter of the spherical enlargement 28 of the ring is chosen to be greater than the diameter of the cylindrical lateral portions 22 of the interior cavity 20 but less than the diameter of each of the central portion 21. In this way, at rest, the ring 24 is trapped with clearance formed by the interior cavity 20.

Note further that the limitation of angular movement of the ring 24 by the annular abutments formed by each externally cylindrical portion 29 guarantees that the interior passage 26 in the ring 24 is correctly aligned with the entry of the cavity 20 of the clamp 9. The possible angle of rotation of the rod 27 about the axis of the interior cavity 20 defined in this way is preferably about 15° as shown in FIG. 2.

Screwing the nut 5 onto the screwthreaded upper portion head 3 clamps the upper branch 11 and the lower branch 10 of the clamp 9 which, in turn, compresses the ring 24 into the two sharp edges 23. Because of the flexibility of the ring 24, imparted by the slot 25 and the groove 30, the ring 24 in turn clamps the connecting rod 27, which is firmly locked in the position chosen by the practitioner. Note here that the fact that the clamp 9 bears on the ring 24 along two sharp edges 23 assures locking of excellent quality. The quality of locking can be further improved by at least partly roughening the surface of the ring 24, the passage 26 through the ring 24, and the surface of the connecting rod 27 if appropriate, for example by sandblasting or machining.

In a variant of the part from FIGS. 3 through 5 shown in FIGS. 9 and 10 the orifices 17, 18 of the branches 10, 11 are of oblong shape in the longitudinal direction of the branches of the device. Further, the external face of the upper branch 11 has a straight step 14' delimiting a recessed area 32. A flat nut (not shown) is partially housed in the recessed area 32. The step 14' is at a sufficient distance from the flat nut to enable it to be turned with a wrench. This oblong variant allows the distance between the axis of the connecting rod 27 and that of the screwthreaded upper portion head 3 to be varied, enabling adaptation to the various morphotypes encountered, and, in conjunction with the orientation possibilities, limitation of the degree of curvature of the rods.

In another variant, not shown, the clamp 9 is provided over part of its extent with lower and upper median slots to enhance its elastic deformability.

Finally, the invention is not limited to the embodiments described hereinabove but to the contrary encompasses all variants thereof. In particular, these spinal instruments can be associated with plate type instruments as described in patent FR-B-2 657 775.

I claim:

1. A spinal instrument for essentially smooth adjustable connecting rods, the spinal instrument comprising:

a nut (5);

a bone anchor member (1) having an anchor portion (2) separated from a projecting screwthreaded head (3) by an intermediate body (4) having a polygon section (19) with an upper portion, the upper portion of which forms an abutment (7), the projecting screwthreaded head (3) being associated with the nut (5); and a receiving and locking assembly (8), the assembly (8) having a clamp (9) and a compressible ring (24), the clamp (9) having a lower branch (10) and an upper branch (11) linked by a connecting area (12), the lower branch (10) and the upper branch (12) each being provided with an orifice (17) and orifice (18), respectfully, the lower branch orifice (17) aligned to the upper branch orifice (18) so that the projecting screwthreaded head (3) can be passed therethrough as far as the abutment (7), the connecting area (12) of the clamp (9) delimiting a cavity (20) between the lower branch (10) and the upper branch (11), the compressible ring (24) housed in the cavity (20), the compressible ring (24) having a central passage (25) to receive the connecting rod, the receiving and locking assembly (8) forming a ball joint so that the clamping of the lower branch (10) and the upper branch (11) by the nut (5) engaged on the screwthreaded head (3) locks the compressible ring (24) and the connecting rod in the required angular position.

2. The spinal instrument of claim 1, the cavity (20) having at least one sharp edge (23) adapted to load the compressible ring (24) during damping.

3. The spinal instrument of claim 2 wherein only the at least one sharp edge (23) of the clamp cavity (20) is adapted to bear on the compressible ring (24) during clamping.

4. The spinal instrument of claim 2 wherein the at least one sharp edge (23) is two sharp edges (23) and only the two sharp edges (23) of the clamp cavity (20) is adapted to bear on the compressible ring (24) during clamping.

5. The spinal instrument of claim 1, the cavity (20) having a cylindrical central portion (21) flanked on opposite sides by two cylindrical lateral portions (22), each cylindrical lateral portion (22) being coaxial with the cylindrical central portion (21) and having a smaller diameter than the diameter of the cylindrical central portion (21) so as to form a step having two circular sharp edges (23) that face one another.

6. The spinal instrument of claim 5, each cylindrical lateral portion (22) having an external edge (33) that is chamfered.

7. The spinal instrument of claim 5 wherein the compressible ring (24) is an annular shaped ring having a convex external face (28) formed within a diameter that is less than the diameter of the cylindrical central portion (21) and is greater than the diameter of each cylindrical lateral portion (22).

8. The spinal instrument of claim 7 wherein the convex external face (28) of the ring (24) is spherical.

9. The spinal instrument of claim 7, wherein the convex exterior face (28) of the ring (24) is extended on each side by cylindrical portions (29) forming angular movement limitation abutments.

10. The spinal instrument of claim 1, the compressible ring (24) further having a through-slot (25).

11. The spinal instrument of claim 10, the compressible ring (24) further having a convex exterior face (28), the convex exterior face (28) of the compressible ring (24) having a groove (30) that is symmetrical to the through-slot (25) about the axis of the compressible ring (24).

12. The spinal instrument of claim 1 wherein the angle of the axis of the compressible ring (24) relative to the axis of the cavity (20) at rest is limited.

13. The spinal instrument of claim 1, the polygon section (19) of the bone anchor member (1) having at least one vertical face, the lower branch (10) of the clamp (9) further having a step (13) against which a vertical face of the polygon section (19) can bear to block the relative rotation of the bone anchor member (1) and the clamp (9).

14. The spinal instrument of claim 1, the nut (5) having a spherical convex lower face (31), the upper branch (11) of the clamp (9) further having a spherical concave area (16) in which the spherical convex lower face (31) of the nut (5) is housed.

15. The spinal instrument of claim 1 wherein the orifices (17, 18) are of oblong shape in the longitudinal direction so as to vary the distance between the axis of the connecting rod and the axis of the screwthreaded head (3).

16. The spinal instrument of claim 1, the upper branch (11) of the clamp (9) further having a step (14') producing a recessed area (32) in which the nut (5) is at least partially housed.

17. The spinal instrument of claim 1 wherein the surface of at least one of the cavity (20) and the compressible ring (24) is a rough surface.

* * * * *

UNITED STATES PATENT AND TRADEMARK OFFICE
CERTIFICATE OF CORRECTION

PATENT NO. : 5,938,663
DATED : August 17, 1999
INVENTOR(S) : Petreto

It is certified that error appears in the above-identified patent and that said Letters Patent is hereby corrected as shown below:

Column 5,
Line 31, delete "during damping" and insert -- during clamping --.

Signed and Sealed this

Twenty-eighth Day of August, 2001

Attest:

*Nicholas P. Godici*

NICHOLAS P. GODICI
*Attesting Officer*   *Acting Director of the United States Patent and Trademark Office*